United States Patent [19]

Smith

[11] 3,979,506
[45] Sept. 7, 1976

[54] RADIOACTIVE COMPOUNDS FOR LABELING PROTEINS
[75] Inventor: Paul K. Smith, Rockford, Ill.
[73] Assignee: Pierce Chemical Company, Rockford, Ill.
[22] Filed: Oct. 11, 1974
[21] Appl. No.: 514,139

[52] U.S. Cl. .................. 424/1; 260/429 R; 260/453 RW; 260/465 R
[51] Int. Cl.² .............. A61K 43/00; C07C 119/00; C07C 122/00
[58] Field of Search..... 260/453 RW, 465 R, 429 R; 424/1

[56] References Cited
UNITED STATES PATENTS
3,444,236   5/1969   Nishizawa et al. ............... 260/465 R

OTHER PUBLICATIONS

Bolton et al., Bio. Chem. Journal, No. 133, 1973, pp. 529–539.

Nuclear Science Abstracts, vol. 28, No. 8, Oct. 31, 1973, p. 1696, Item No. 17978.

*Primary Examiner*—Benjamin R. Padgett
*Assistant Examiner*—Christine M. Nucker

[57] ABSTRACT

New radioactive compounds are disclosed which are useful for labeling proteins and the like for radioimmunoassay techniques. These compounds are imido esters of radioactive substituted hydroxy or alkoxy phenyls.

11 Claims, No Drawings

RADIOACTIVE COMPOUNDS FOR LABELING PROTEINS

The present invention relates to the radioactive labeling of proteins and the like and, more particularly, to new compounds which can be used for this purpose.

Proteins labeled with radioactive isotopes such as radioactive iodine ($^{125}$I) are useful in biochemical studies, particularly in radioimmunoassay techniques. For a number of years the chloramine-T procedure has been used which involves reaction of radioactive sodium iodide, in the presence of a mild oxidant such as chloramine-T, with the tyrosyl residue of a protein. This direct labeling procedure, however, is accompanied by the disadvantage that the protein being studied is frequently altered or seriously damaged. Furthermore, the chloramine-T procedure is only applicable with respect to proteins which have tyrosine and, accordingly, its utility is somewhat limited.

Recently, a procedure has been developed for labeling proteins with radioactive iodine in which the protein itself is not directly exposed to an iodine solution or to the reagents used in the iodination reaction. Bolton and Hunter, Biochem. J. (1973)133, pp. 529–539. According to this procedure, the protein is reacted under mild conditions with the N-hydroxysuccinimide ester of 3-(4-hydroxyphenol) propionic acid which has been previously labeld with $^{125}$I and separated from the products of the iodination reaction by solvent extraction. The hydroxysuccinimide esters react with free amino groups of proteins or peptides to form amides. This new method is stated as having the advantage that the radioactive iodine label is introduced into a group other than the tyrosine residue so that an alternative form of chemical modification to that generally employed heretofore is available.

While the method using the succinimide ester has advantages over the direct iodination of the protein, there are, nevertheless, drawbacks associated with this method. Iodination is ordinarily accomplished in an aqueous solution and, because of the instability of the hydroxysuccinimide ester under the conditions of iodination, the procedure must be carried out very rapidly in order to achieve good yield of the iodinated product. Generally, the time taken from the addition of radioactive sodium iodide to recovery of the product in non-aqueous form cannot exceed about 20 seconds or very low yields will be obtained. Even with a very fast procedure, e.g., about 10 seconds, yields in excess of about 75 percent are not obtainable. Furthermore, the use of succinimide esters is believed to alter the charge on the labeled protein which, in certain instances, may be undesirable.

Now, in accordance with the present invention new radioactive compounds are provided which can be used for labeling proteins and the like which have the heretofore discussed advantages associated with the use of succinimide esters, but which can be easily prepared in high yield and which can be used to prepare labeled proteins without altering protein charge. The compounds so provided are imido esters of radioactive substituted hydroxy or alkoxy phenyls and can be represented by the structural formula

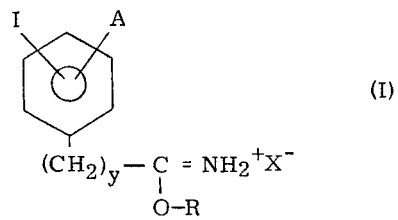

(I)

wherein I is a radioactive isotope; A is hydroxy or an alkoxy group; y is an integer; R is an alkyl group; and X is a halogen.

Preparation of the above illustrated compounds can be readily accomplished by known techniques and in especially high in yield, e.g., substantially stiochiometric, at all stages. Initially, a radioactive salt such as NaI is reacted with a hydroxy or alkoxy phenyl nitrile to yield the corresponding radioactive substituted nitrile compound. The reaction readily proceeds in a buffered (about pH 7.5) aqueous solution at room temperature in the presence of an oxidizing agent such as chloramine-T. The nitrile intermediate, which is also new and thus provided by the present invention, has the structural formula

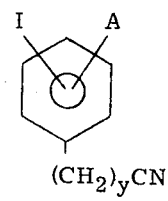

(II)

The imido ester (formula I) can be prepared by reacting the nitrile (formula II) with a monofunctional alcohol in the presence of an inorganic acid and solvent at, for example, 0°C. Subsequent reaction of the radioactive imido ester with protein amine groups (amidation) can be effected in aqueous solution. General techniques of imido ester formation and amidation are discussed in "Methods of Enzymology", Vol. XXV, Enzyme Structure, Part B, Ed. Hirs and Timasheff, Ac. press, (1972), pp. 585–596.

With reference to the foregoing compounds (formulas I and II) is preferably radioactive iodine ($^{125}$I) and, due to ease of preparation, X is generally Cl. As to the parameters A and y, their selection is not especially critical so long as the phenyl group is rendered sufficiently electropositive so as to facilitate iodination. To this end, A is preferably para-positioned relative to the ester moiety and a hydroxy or an alkoxy group having, for example, 1–5 carbon atoms and particularly methoxy or ethoxy. Similarly y can be a small integer, e.g., less than 10, such as 1, 2 or 3. The alkyl group, R, being derivable from the alcohol used in preparing the imido ester, is similarly not particularly critical. Since lower alcohols, e.g., those having less than about 10 carbon atoms, are most easily used in the ester forming reaction, R preferably is an alkyl group with less than about 10 carbon atoms. Methyl and ethyl groups are especially preferred.

EXAMPLE

About 1.0 equivalents of p-hydroxyphenylpropionitrile and about 1.5 equivalents of KI containing a desired level of K$^{125}$I is suspended in about 0.25M phosphate buffer pH 7.5. Mixing is accomplished in an ultrasonic bath at room temperature. To the agitated suspension is added at once about 2.0 equivalents of chloramine-T in 0.25M phosphate buffer, pH 7.5. The reaction mixture is then quenched by addition of 2 equivalents of sodium metabisulfite in pH 7.5 phosphate buffer to destroy unreacted iodine and chloramine-T. Agitation is discontinued and the resulting iodinated product is extracted in benzene. The benzene layer is dried with anhy calcium chloride and added to an anhydrous methyl alcohol solution at 0° containing at least 1.0 equivalents of disolved HCl. The resulting solution now containing an iodinated imidoester compound may be used directly for derivatizing protein in the usual manner. The foregoing reaction sequence can be represented as follows:

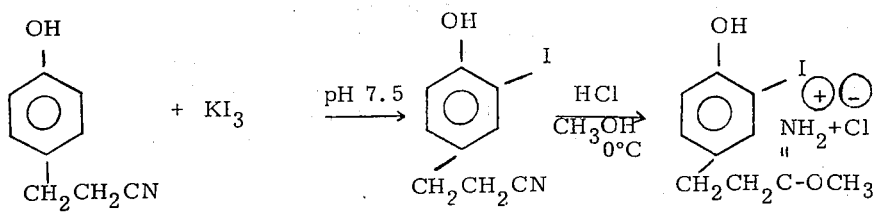

I claim as my invention:
1. A compound having the structural formula

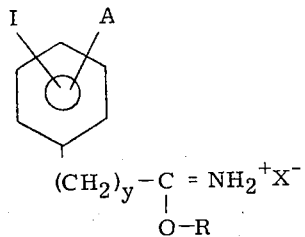

wherein I is a radioactive isotope; A is hydroxy or an alkoxy group; y is an integer; R is an alkyl group; and X is a halogen.

2. The compound of claim 1 wherein I is radioactive iodine, A is hydroxy, y is an integer of less than 10, R is an alkyl group having less than about 10 carbon atoms, and X is Cl.

3. The compound of claim 2 wherein y is 1, 2 or 3, R is methyl or ethyl, and A is para-positioned relative to the ester group.

4. The compound of claim 3 wherein y is 2 and R is methyl.

5. A compound having the structural formula

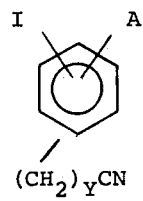

wherein I is a radioactive isotope; A is hydroxy or an alkoxy group and y is an integer.

6. The compound of claim 5 wherein I is radioactive iodine, A is hydroxy and y is 1, 2 or 3.

7. The compound of claim 6 wherein y is 2 and A is para-positioned relative to the nitrile group.

8. A process for labeling a protein with a radioactive isotope comprising reacting, in an aqueous medium, amine groups of a protein with a compound of claim 1.

9. A process for labeling a protein with a radioactive isotope comprising reacting, in an aqueous medium, amine groups of a protein with a compound of claim 2.

10. A process for labeling a protein with a radioactive isotope comprising reacting, in an aqueous medium, amine groups of a protein with a compound of claim 3.

11. A process for labeling a protein with a radioactive isotope comprising reacting, in an aqueous medium, amine groups of a protein with a compound of claim 4.

* * * * *